United States Patent [19]

House

[11] 4,365,626
[45] Dec. 28, 1982

[54] UNIVERSAL SYRINGE

[76] Inventor: Hugh A. House, 159 Lincoln Rd., Wenonah, N.J. 08090

[21] Appl. No.: 281,842

[22] Filed: Jul. 9, 1981

Related U.S. Application Data

[63] Continuation-in-part of Ser. No. 88,141, Oct. 25, 1979, abandoned.

[51] Int. Cl.³ .............................................. A61M 5/00
[52] U.S. Cl. .......................... 128/218 DA; 128/218 N
[58] Field of Search ....... 128/218 R, 218 D, 218 DA, 128/220, 221, 215, 216, 218 P, 218 N, 218 NV

[56] References Cited

U.S. PATENT DOCUMENTS 3,757,780  9/1973  Ishikawa .............................. 128/221
3,989,044  11/1976  Meierhofer ...................... 128/218 N Primary Examiner—John D. Yasko
Attorney, Agent, or Firm—Omri M. Behr

[57] ABSTRACT

A universal syringe includes a sterile filled glass vial of injectable medicament retained within the vial by identical piston seals disposed proximate each cylinder end. The piston seals are in intimate frictional contact with the internal walls of the vial and are slidable therealong. Removable plastic end caps are removably retained on the vial ends to maintain the vial in a sterile condition until used. A slidable finger rest encompassing the outer wall of the vial is movable therealong and retained by externally protruding lip portions provided on both ends of the vial. A needle assembly is removably retained in a hollow cylindrically shaped piston rod which is capped on both ends to maintain the sterile condition. The needle assembly may be readily removed from the hollow piston rod and one end thereof may be inserted into the vial piston seal at either end and retained thereby, a needle pierced the seal to provide communication of the medicament in the vial through the needle opening to the patient. The piston rod may be inserted into the remaining vial seal and be retained thereby, thus providing a complete syringe.

10 Claims, 15 Drawing Figures

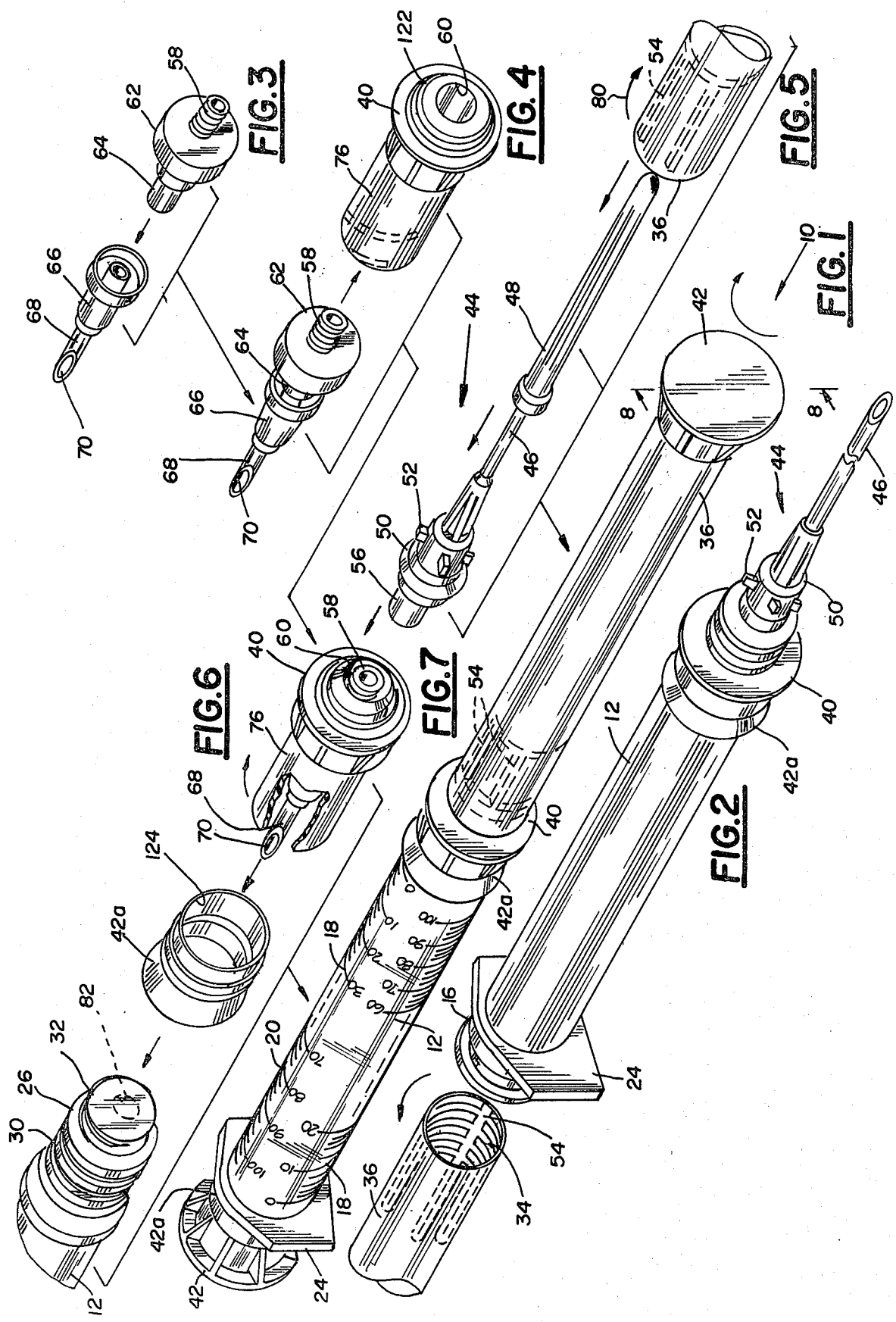

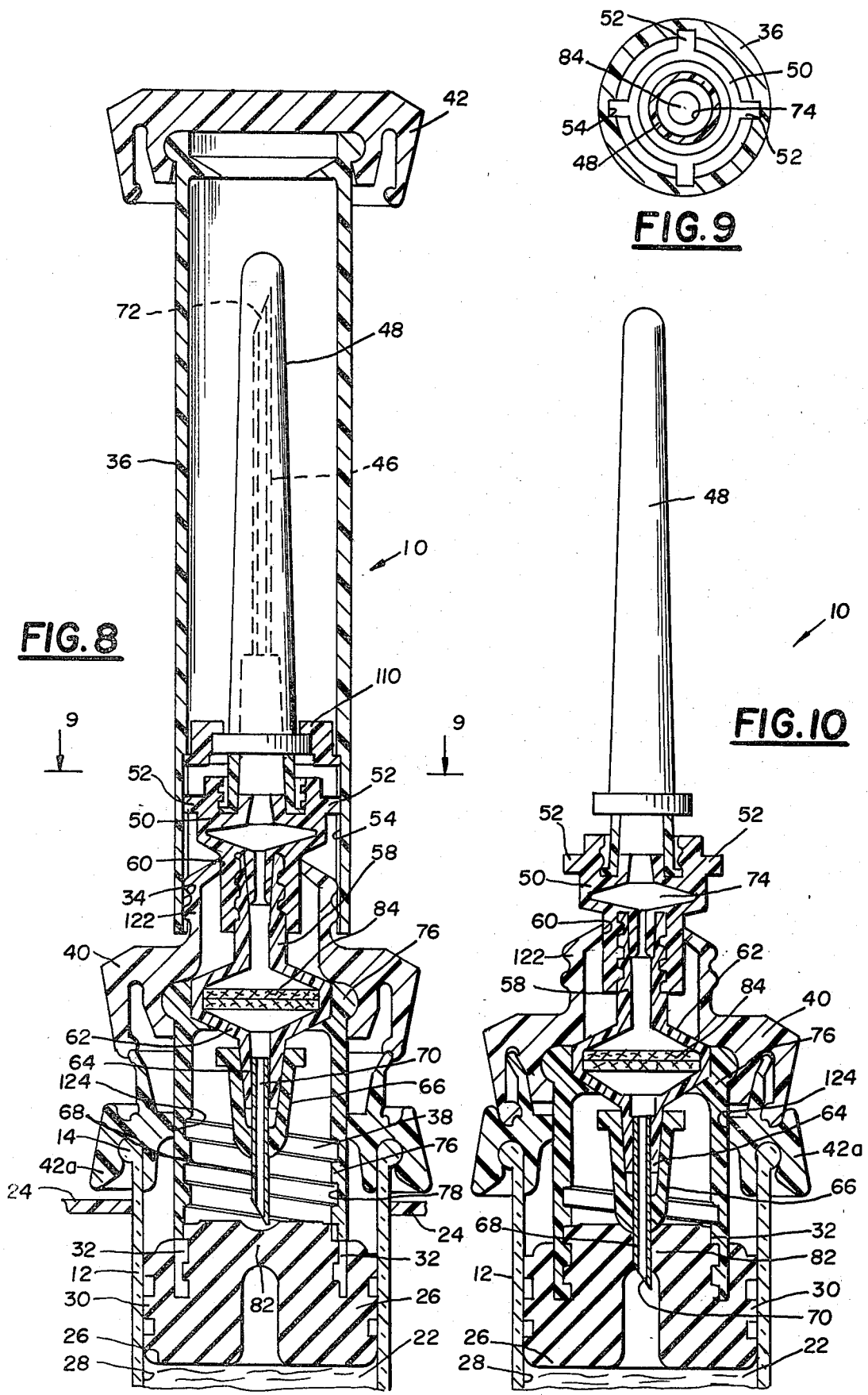

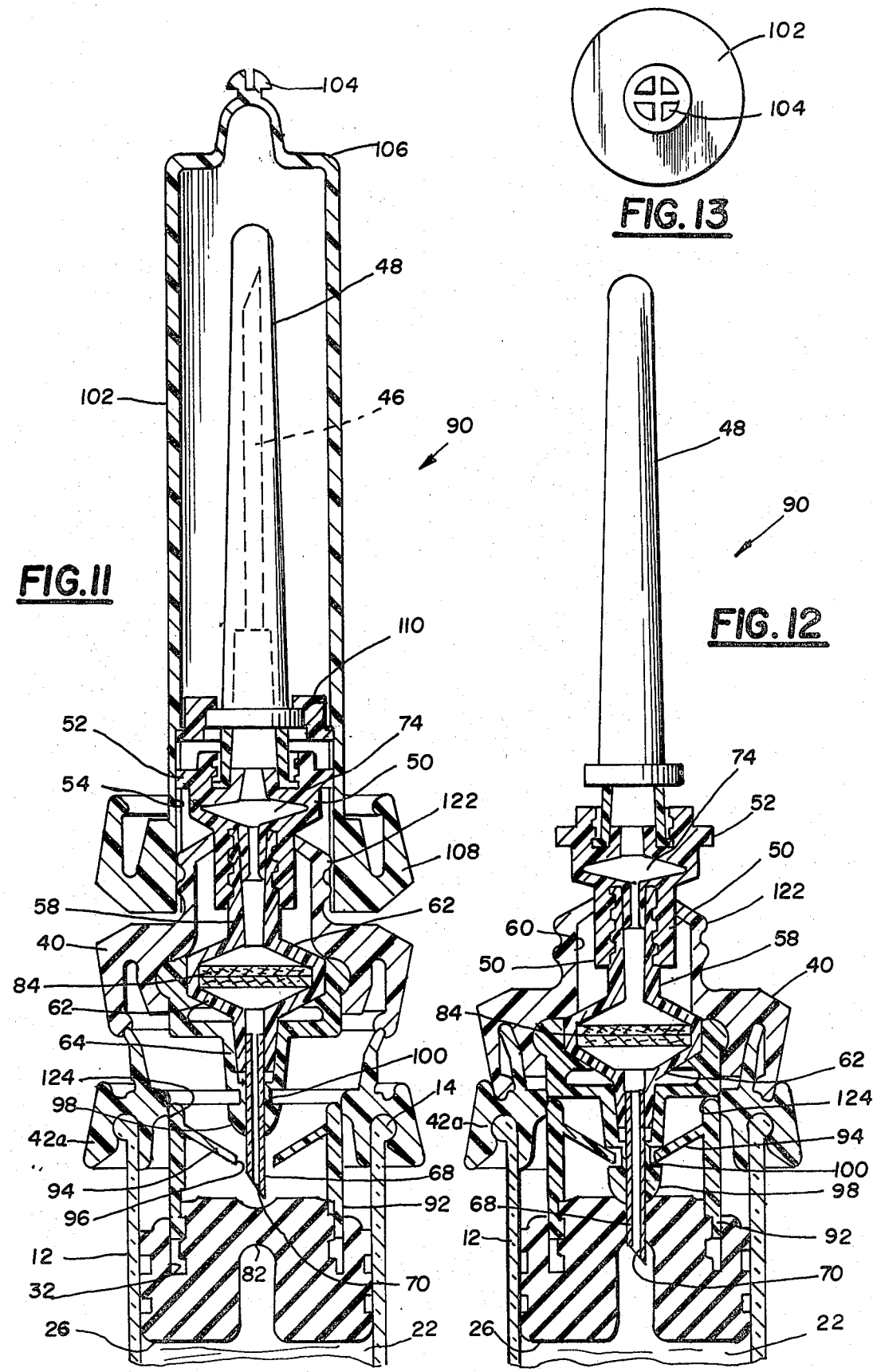

UNIVERSAL SYRINGE

This is a continuation-in-part-application of previously filed application Ser. 88,141 filed on Oct. 25, 1979 and entitled "Sterile Injecting Syringe-Vial" now abandoned.

BACKGROUND OF THE INVENTION

1. Field of the Invention

The present invention relates to hypodermic syringes, and in particular, to a universal syringe ideally suited for emergency use situations where the speed of assembling of the sterile components parts is critical.

2. Background of the Invention

The prior art abounds with designs for hypodermic syringes and needle assemblies, particularly of the type wherein the medicament retaining vial is inserted into one end of a syringe barrel and a transfer-needle assembly. The syringe plunger urges the vial against the needle piercing portion of the transfer needle and permits the medicament to flow from the vial to the needle piercing assembly and transfer needle. This type of arrangement is disclosed in U.S. Pat. No. 3,884,229 issued to Raines, et al on May 20, 1975. The medicament holding vial disclosed therein has a plunger proof seal on one end thereof and a piercable seal on the other end and is positioned so that the piercing needle is accurately aligned to the center of the seal while the other end is provided with a plunger with which the user provides the necessary pressure to force the vial against the piercing needle, thereby, permitting the medicament, once the seal in the valve is pierced, to communicate through the needle piercing aperture to the transfer needle and, thus into the patient.

Another syringe utilizing a pre-filled vial which has one end of the vial sealed by means of a rubber diaphragm and the other end thereof sealed by a stopper is disclosed in U.S. Pat. No. 3,989,044 issued to Meierhoefer on Nov. 2, 1976. A needle hub assembly associated with the vial is used to pierce the stopper, thereby permitting the medicament contained within the vial to communicate with the transfer needle, and thus, into the patient.

The shortcomings of the prior art devices are overcome by the instant invention since the instant invention uilizes a vial which is identical on both ends and may be used interchangably, thereby providing rapid assembly of a completed syringe for use in emergency situations. Therefore, it is an object of the present invention to provide a universal syringe the elements of which are sterile and may be rapidly assembled in emergency situations.

It is another object of the present invention to provide a universal syringe which includes a vial that contains a liquid medicament and is identical on each end thereof.

It is yet another object of the present invention to provide a universal syringe for the application of liquid medicaments wherein the vial is adapted to receive the needle assembly in one end thereof and is adapted to receive the piston rod in the other end thereof. It is yet another object of the present invention to provide a universal syringe which utilizes the piston rod to store the needle assembly prior to use.

It is yet another object of the present invention to provide a universal syringe wherein the protective cap includes a piercing needle adapted to be received by the piston seal and the other end includes a micropore filter and is adapted to receive a needle for insertion into a patient.

The foregoing and other objects and advantages will appear from the description to follow. In the description, reference is made to the accompanying drawing which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

SUMMARY OF THE INVENTION

A universal syringe, according to the principles of the present invention, for the application of liquid medicaments comprises, in combination, an elongated cylindrical-shaped vial having outwardly extending lip portions proximate each end thereof and identical piston seals disposed proximate each cylinder end. The piston seals are in intimate frictional contact with the internal walls of the vial and are slidable therealong. The vial is adapted to retain the liquid medicament between the piston seals. A slidable finger rest encompasses the outer wall of the vial and is movable therealong until restrained by the lip portions. A cap is adapted to be received on each end of the vial to maintain its sterility. A needle assembly includes a needle having one end adapted to be inserted into a patient and the other end thereof adapted to be removable retained by either of the vial lip portion while piercing the piston seal and communicating with the medicament disposed from within the vial. A hollow, elongated, cylindrically-shaped piston rod is adapted to removably receive the needle therein. When the needle is removed from the piston rod after being inserted into a piston seal the piston rod is adapted to be received by the remaining piston seal and functions as a piston rod.

BRIEF DESCRIPTION OF THE DRAWING

In order that the invention may be more fully understood, it will now be described, by way of example, with reference to the accompanying drawing in which:

FIG. 1 is a perspective view of a fully assembled syringe, according to the principles of the present invention;

FIG. 2 is a perspective view of the syringe with the piston rod in position ready to be received by a piston seal;

FIG. 3 is an exploded view in perspective showing the relative position of the piercing needle and the micropore filter;

FIG. 4 is an exploded view in perspective showing the piercing needle and filter assembled and with the multidose vial adaptor in position to receive the opposite end of the micropore filter;

FIG. 5 is an exploded view in perspective of the patient or transfer needle and needle cover in position to be received by the hollow piston rod on one end thereof;

FIG. 6 is a perspective view of the piercing needle and filter assembly with the multidose vial adaptor in position to receive the patient needle therein on one end and in position to be received by a piston seal on the other end;

FIG. 7 is an exploded perspective view of the universal syringe including the medicament vial, multidose vial adaptor, needle piercing and filter assembly, seal adaptor, and piston seal together with the patient needle adaptor, patient needle, needle cover and portion of the hollow piston rod;

FIG. 8 is a partial cross-sectional view in elevation taken along the line 8—8 of FIG. 1 showing the leading end of the syringe in a fully assembled position prior to penetration of the piston seal by the piercing needle;

FIG. 9 is a view taken along the line 9—9 of FIG. 8;

FIG. 10 is a partial cross-sectional view in elevation of the leading end of the fully assembled syringe with the piston rod removed and the piercing needle completing penetration of the piston seal for withdrawal of the liquid medicament;

FIG. 11 is a partial cross-sectional view in elevation of an alternative embodiment of the universal syringe shown in the leading end thereof, fully assembled prior to penetration of the piston seal by the piercing needle;

FIG. 12 is a partial cross-sectional view in elevation of the embodiment shown in FIG. 11 with the piercing needle penetrating the piston seal for the withdrawal of the liquid medicament;

FIG. 13 is a top plan view of one end of the piston rod shown in the configuration disclosed in FIG. 11;

DESCRIPTION OF THE PREFERRED EMBODIMENTS

Figure 14:
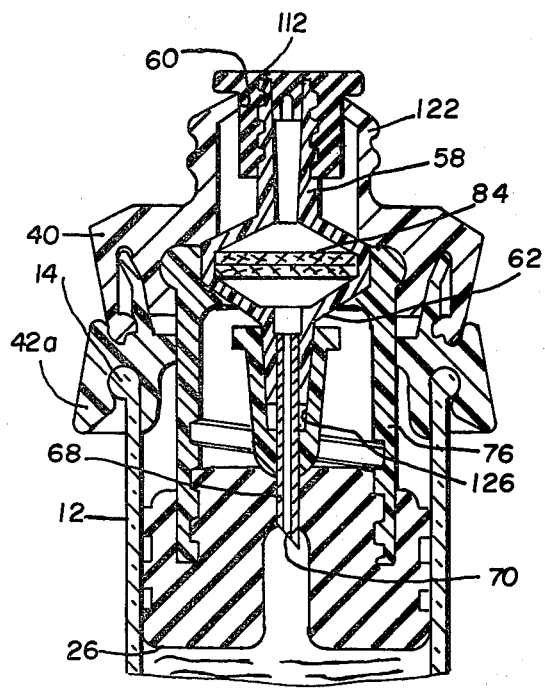
FIG. 14 is an enlarged partial cross-sectional view of the embodiment shown in FIG. 10 with the piston rod and patient needle removed and replaced with an insert to maintain sterility.

Referring now to the figures, and in particular to FIG. 1, there is shown a perspective view of the fully assembled universal syringe 10 which includes an elongated cylindrically-shaped vial 12, preferably made of glass, and having outwardly extending protrusions or lip portions 14 and 16 provided at the distal ends thereof (see FIG. 8). The surface of the vial 12 is provided with indicia 18 and 20 in the form of scale graduations starting at zero at one end and reaching 100 at the opposite end. At the same time, indicia is provided thereon starting at 100 at the same end and reducing to zero at the opposite end. The function of the indicia provided on the vial 12 will become obvious hereinafter and is an indication of the amount of medicament 22 remaining in the vial. A slidable finger rest 24 encompasses the surface of the vial and may be moved from one end thereof to the other being restrained by the extending lip portions 14 or 16 at the convenience of the individual utilizing it.

An identical pair of piston seals 26 are disposed within either end of the vial 12 and are in frictional intimate contact with the inner wall 28 of the glass vial 12 in order to contain the medicament 22 which is in liquid form therebetween. The circumference of the piston seal 26 is provided with a plurality of ridges 30 which permit the piston seal 26 to move freely along the inner wall 28 of the vial while preventing the liquid medicament from leaking therearound. In the embodiment disclosed in FIG. 8, the piston seals 26 are provided with a threaded channel 32 circumferentially disposed and proximate to the periphery of the piston seal 26. The threaded groove is adapted to receive and cooperate with a mating thread 34 provided on the piston rod 36 (see FIG. 8) in addition to the mating thread 38 provided on the vial-adaptor 40 (FIG. 4) as will be explained hereinafter. Thus, the glass vial may receive the piston rod 36 on either end and is also capable of receiving the vial adaptor on either end. Since each of them are capable of being received into either of the threaded channels 32 provided in the piston seals 26, they permit an individual to assemble the universal syringe in a more rapid-like manner than possible before.

A pair of end caps or seals 42 and 42a are provided on each end of the vial 12 in order to maintain sterility of the contents thereof.

The piston rod 36 is adapted to receive a needle assembly 44 which includes patient or transfer needle 46 and a needle cover 48. The transfer needle 46 includes a shoulder portion 50 which is provided with a plurality of outwardly extending protrusions 52 adapted to cooperate with and extend into grooves 54 provided in the hollow piston rod 36 as shown in FIGS. 5 and 8. The other end of the needle assembly 44 proximate the shoulder portion 50 is provided with a conically shaped internally threaded portion 56 which is adapted to be received by an externally threaded mating portion 58 provided on the vial adaptor 40 (see FIGS. 7 and 8). The portion 58 extends through the opening 60 and is one end of a micropore filter 62 disposed in the vial adaptor. The other end of micropore filter 62 is provided with a conically shaped protruding portion 64 having a shoulder 66, a piercing needle 68 cooperating therewith and removably affixed thereon in a conventional manner, as shown in FIGS. 3, 4 and 8. The piercing needle 68 is provided with an aperture 70 permitting communication therethrough into the micropore filter and through the vial adaptor to the aperture 72 provided in the patient or transfer needle 46. A chamber 74 is provided between the micropore filter and the patient transfer needle in the shoulder portion 50 of the transfer needle 46 in order to permit the user of the syringe to see that the transfer needle 46 has entered a vein or artery of the patient by permitting blood that has entered the chamber to be visible to the user of the syringe. Thus, the syringe user is assured of application of the medicament in the syringe directly into the patient's vein or artery.

A portion 76 of the vial adaptor extends outwardly at the opposite end from the threaded portion 58 of filter 62 and is adapted to completely encompass the filter therein and extend beyond the opposite end of the filter with internally provided threads 78 provided therein to cooperate with and engage the threaded channel 32 provided in the piston seal 26 and as the threads 32 and 78 engage and cooperate as the piston rod is rotated in the direction of arrow 80 (FIG. 5) the piercing needle 68 pierces the narrow portion 82 provided in the piston seal 26 as shown more clearly in FIG. 10.

FIG. 2 shows the vial 12 with the needle assembly 44 in position on the vial 12 and with the cover 48 or the patient or transfer needle 46 exposed. The finger rest 24 has been moved into position for use and the piston rod 36 is about to be inserted into a piston seal for use as a completed syringe. The actual assembly procedures will be outlined hereafter in conjunction with FIG. 7 which shows the steps in assembling the completed universal syringe.

FIG. 9 is a view taken along the line 9—9 of FIG. 8 and more clearly shows the grooves 54 provided in the internal wall of the hollow piston rod 36 cooperating with the protrusions provided on the shoulder portion 50 of the transfer needle. The micropore filter elements 84 may be seen to close off the aperture 72 of the transfer needle 46 and prevent foreign matter from entering into the aperture 70 provided in the piercing needle 68.

FIG. 10 is a cross-sectional view showing the piercing needle in its final or rest position wherein it has pierced the narrow portion 82 of the piston seal 26, thereby permitting the medicament 22 disposed in the vial 12 between the end seals 26 to communicate, via the aperture 70, filter 84, chamber 74 and aperture 72 in the transfer needle 46 to the patient who is to receive the medicament. The piercing of the narrow portion 82 of piston seal 26 is accomplished by the rotation of the piston rod 36 in the direction of arrow 80 (FIG. 5) taking with it the micropore filter 62, and piercing needle 60 by permitting the extending portion 76, which is internally threaded to engage the threaded channel 32 of the piston seal and advance in a downwardly direction with each rotation until the narrow portion of the seal is pierced.

FIG. 11 is an alternative embodiment 90 of the universal syringe described in FIG. 8. Like components have been given like numerical designations for clarity and will be maintained throughout the remaining figures. The vial 12 includes a pair of piston seals 26, preferably fabricated of rubber (only one being shown in this embodiment as was shown in FIG. 8). The seal 26 is provided with a threaded channel 32 which is adapted to receive therein the extending portion 92 of the vial adaptor 40. The extending portion 92 is provided with a plurality of inwardly extending portions 94, preferably three, which has centrally disposed opening 96 adapted to receive a hemispherically-shaped shoulder portion 98 therein. When the hemispherically-shaped portion 98 is forced into the opening 96 the inwardly extending portions 94 are retained in a channel 100 which extends circumferentially just behind the shoulder portion 98, thereby retaining the shoulder in a relatively fixed position which may only be removed by exerting a relatively large force therebetween. A piercing needle 68 is centrally disposed in the shoulder portion 98 in a conventional manner. Holding the vial in one hand and applying pressure to the piston rod 102 will cause the shoulder portion 98 to enter aperture 96, thereby permitting the piercing needle 68 to puncture the narrow portion 82 of the seal 26 providing communication with the liquid medicament 22 disposed within the vial 12 between seals 26. At the same time that the piercing needle 68 punctures the seal 26 vial, adaptor 40 is caused to engage the end cap 42a further adding to the security and retention of the piercing needle in position. The vial adaptor 40 has inserted therein the micropore filter 62 in the same manner as described in the earlier embodiment.

The piston rod 102 is provided with a shoulder portion 104 at its distal end 106 which is identical to shoulder portion 98 provided on the portion 64 of vial adaptor 40, thereby permitting the piston rod distal end 106 to be inserted into the extending portion 92 of the end cap 42a. A cap 108 is provided on the filter end of the piston rod 102 and positioned such that when the piston rod is inserted into piston seal 26 and pressure has been exerted thereon to completely expend the medicament from vial 12, cap 108 will be retained by the lip portion 16 as shown in FIGS. 8 and 10, thereby indicating to the user that the medicament has been completely expended from the vial. An internal shoulder 110 is provided in the piston rod 102, as well as, in piston rod 36 to enable the needle cover 48 to remain in position and complete the seal and, thereby, avoid contamination of the transfer needle 46.

FIG. 12 is a cross-sectional view which shows the position of the components after the piercing needle 68 has pierced the seal 26. The piston rod is removed exposing the needle cover 48 which functions to protect the transfer needle 46. The piston rod 102 is now available for insertion into the opposite end of the vial 12.

FIG. 13 is a top or plan view of the piston rod 102 showing the shoulder portion provided thereon.

Figure 15:
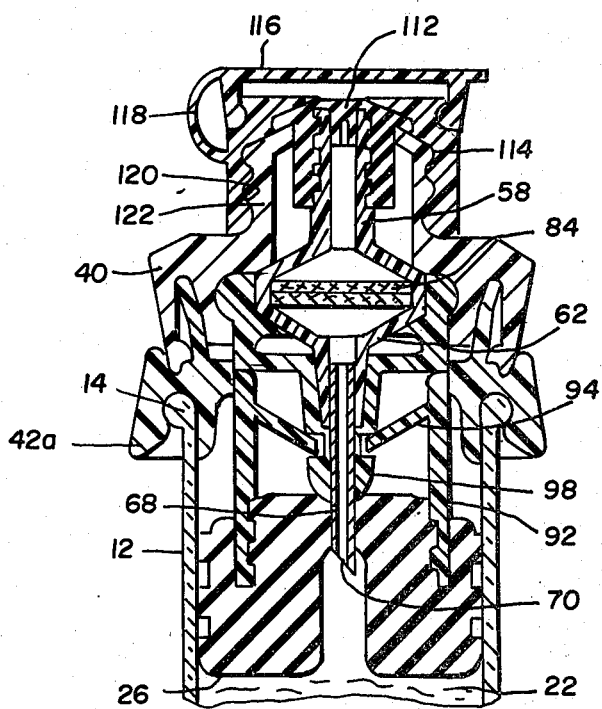
FIG. 15 is an enlarged cross-sectional partial view in elevation of the embodiment shown in FIG. 12 with the piston rod and patient needle removed and replaced by a cap over the insert and micropore filter assembly in order to maintain sterility of the medicament vial.

FIG. 14 is an enlarged partial cross-sectional view of the embodiment described in conjunction with FIG. 10 with the patient transfer needle 46 removed from the vial adaptor. An adaptor plug 112 may be inserted into the opening 60 left remaining by the removal of the transfer needle exposing the portion 58 of the micropore filter 62. By going one step further, as shown in FIG. 15, and providing a sealing cap 114 with a pop-off cover 116, the sealed integrity of the system may be maintained. The cover 116 may include a living hinge 118 attaching the cover to the sealing cap so that it may be repeatedly re-used. Thus, a unitary sealing cap and cover arrangement may include a micropore filter and provide communication into the medicament in the vial and yet be maintained in a sealed sterile relationship. The adaptor plug 112 is, preferably, made of a rubber material which may be readily threaded on the threaded portion 58 of the micropore filter 62 and is readily deformed when the sealing cap 114 is threaded on to the threads 120 on the outwardly extending portion 122 of the vial adaptor 40. As shown, the sealing cap 114 may be used on either of the disclosed embodiments.

In operation, the prefilled syringe vial 12 is assembled in a sterile environment and filled with the medicament 22 and is provided with a pair of end caps 42 disposed on either end to maintain the integrity of the vial. The vial adaptor 40 together with the patient needle 46 and needle cover 48 is snapped into place in the piston rod 36 by means of the grooves 54 provided therein which cooperates with the protrusions 52. By rotating the piston rod 36 the internally provided threads of the portion 56 of shoulder portion 50 of the patient needle 46 engages the threaded portion 58 provided on the vial adaptor 40, thereby providing a completed assembly. A throw-away cap cover, not shown, is provided to protect the piercing needle 58 and maintain it in sterile integrity until it is ready for use. The end caps or seals provided for the vial 12 includes a throw-away portion 42 and a portion 42a which remains on the vial when it is ready to be used. The end cap 42 is separated from 42a and disposed of, thereby providing an opening 124 through which the extending portions 76 and 92 may enter to engage the channel 32 in the seal 26. Preferably, the piercing needle 68 is provided with a tapered inside diameter 126 (see FIG. 14) which allows for a permanent press fit with a slightly oversized cone-shaped outside diameter of the micropore sterilizing filter 62 so that the upwardly extending portion of the piercing needle 68 functions as a guide and locking wedge as it extends into the cone-shaped inside diameter of the sterilizing micropore filter 62 expanding its sides against the piercing adaptor inner walls. With the construction as disclosed, utilizing the protusions 52 together with the grooves 54 provided in the piston rod 36, when rotating in the direction of arrow 80, permits the patient needle 46 to threadably engage the external threads provided on the micropore filter 62 and permits the threading of the vial adaptor 40 to be threaded on the seals 26. Once the threads or seals 26 have been fully engaged and the piercing needle punctured the seal, the piston rod 36 may be removed by directly pulling it off exposing the needle cover 48. A slight counter-clockwise movement of the piston rod 36, until its thread disengage will remove assembly 44 if desired.

By moving the end cap 42 from the opposite end of the vial 12, the piston rod may be screwed clock-wise into the piston seal 26, thereby completing the assembly of the universal syringe.

Hereinbefore has been disclosed a universal syringe for the application of liquid medicaments which, preferably are prepackaged into separate sterile assemblies and may be integrated into an operational syringe with minimum effort. It will be understood that various changes in the details, materials, arrangement of parts and operating conditions which have been herein described and illustrated in order to explain the nature of the invention may be made by those skilled in the art within the principles and scope of the present invention.

Having thus set forth the nature of the invention, what I claim is:

1. A universal syringe for the application of liquid medicaments comprising, in combination;
    (a) an elongated cylindrically-shaped vial having outwardly extending lip portions proximate each end thereof and identical piston seals disposed proximate each cylinder end, said piston seals being in intimate frictional contact with the internal walls of said vial and slidable therealong, said vial being adapted to retain said liquid medicament therein;
    (b) a slidable finger rest encompassing the outer wall of said vial and movable therealong until restrained by said lip portions;
    (c) cap means adapted to be received on each end of said vial to maintain its sterility; and
    (d) a needle assembly means, said needle assembly means including;
        (i) a needle having one end adapted to be inserted into a patient and the other end thereof adapted to be removably retained by either of said vial lips while piercing said piston seal and communicating with said medicament disposed within said vial, and
        (ii) elongated cylindrically-shaped piston rod means, said piston rod means being hollow and adapted to removably receive said needle therein and when said needle is removed therefrom after being inserted into a piston seal, is adapted to be received by the remaining piston seal to function as a piston rod.

2. A universal syringe according to claim 1 wherein said cap means includes a micropore filter.

3. A universal syringe according to claim 1 wherein said piston seals provided with threaded means proximate the periphery thereof, said threaded means being adapted to receive and cooperate with threaded means provided on said piston rod.

4. A universal syringe according to claim 1 wherein said cap means is provided with retaining means adapted to cooperate with and receive mating retaining means provided on said needle, said mating retaining means and said retaining means being separable.

5. A universal syringe according to claim 1 wherein said cap means includes an elongated piercing means having one end thereof adapted to be received by said piston seal and the other end thereof adapted to receive a micropore filter means.

6. A universal syringe according to claim 1 wherein said piston seals are provided with a centrally disposed retaining means, said centrally disposed retaining means being adapted to receive and cooperate with a mating means provided on said piston rod.

7. A universal syringe according to claim 1 wherein said centrally disposed retaining means is a receptacle having inwardly extending portions and said mating retaining means is provided with an extending portion adapted to be removably retained by said inwardly extending portion when inserted therein.

8. A universal syringe according to claim 1 wherein said needle end adapted to be inserted into a patient is provided with a removable retaining means proximate the shoulder portion thereof, said retaining means being adapted to cooperate with and be removably retained by internal means provided in said hollow piston rod means.

9. A universal syringe according to claim 1 wherein said needle assembly means is provided with an air chamber which, when filled with said medicament prior to application to a patient, is visible to the individual inserting said needle into said patient.

10. A universal syringe according to claim 9 wherein said vial is provided with indicia thereon indicating the amount of medicament remaining in the vial when read from either end.

* * * * *